US006762835B2

(12) United States Patent
Zhang et al.

(10) Patent No.: US 6,762,835 B2
(45) Date of Patent: Jul. 13, 2004

(54) FIBER OPTIC LASER-INDUCED BREAKDOWN SPECTROSCOPY SENSOR FOR MOLTEN MATERIAL ANALYSIS

(75) Inventors: Hansheng Zhang, Aliso Viejo, CA (US); Awadesh K. Rai, Pantnagar (IN); Jagdish P. Singh, Starkville, MS (US); Fang-Yu Yueh, Starkville, MS (US)

(73) Assignee: Mississippi State University, Mississippi State, MS (US)

( * ) Notice: Subject to any disclaimer, the term of this patent is extended or adjusted under 35 U.S.C. 154(b) by 237 days.

(21) Appl. No.: 10/098,368

(22) Filed: Mar. 18, 2002

(65) Prior Publication Data

US 2003/0174325 A1 Sep. 18, 2003

(51) Int. Cl.[7] .................................................. G01J 3/30
(52) U.S. Cl. ...................................................... 356/318
(58) Field of Search ................................ 356/316–318; 156/345.45; 219/121.61

(56) References Cited

U.S. PATENT DOCUMENTS

| | | |
|---|---|---|
| 4,689,467 A | 8/1987 | Inoue |
| 5,085,499 A | 2/1992 | Griffin et al. |
| 5,128,882 A | 7/1992 | Cooper et al. |
| 5,185,834 A | 2/1993 | Day et al. |
| 5,379,103 A | 1/1995 | Zigler |
| 5,608,520 A | 3/1997 | Fleming |
| 5,686,661 A | 11/1997 | Singh et al. |
| 5,751,416 A | 5/1998 | Singh et al. |
| 5,798,832 A | 8/1998 | Hnilica et al. |
| 6,147,754 A | 11/2000 | Theriault et al. |

OTHER PUBLICATIONS

Zhang, H., et al., "Laser–Induced Breakdown Spectrometry As A Multimetal Continuous–Emission Monitor", Appl. Opt. vol. 38, No. 9, pp. 1459–1466, 1999.

Barbini, R., et al., "Semi–Quantitative Time Resolved LIBS Measurements", Appl. Phys B., vol. 65, pp. 101–107, 1997.
Marquardt, B.J., et al., "Novel Probe For Laser–Induced Breakdown Spectroscopy and Raman Measurements Using An Imaging Optical Fiber", Appl. Spectrosc, vol. 52, No. 9, pp. 1148–1153, 1998.
Neuhauser, R.E., et al., "Laser–Induced Plasma Spectroscopy (LIPS): A Versatile Tool For Monitoring Heavy Metal Aerosols", Anal. Chim. Acta, 392, pp. 47–54, 1999.
Neuhauser, R.E., et al., "Utilization of Fiber Optics For Remote Sensing By Laser–Induced Plasma Spectroscopy (LIPS)", Appl Spectrosc., 54, No. 6, pp. 923–927, 2000.
Whitehouse, A.I., et al., "Remote Material Analysis of Nuclear Power Station Steam Generator Tubes by Laser–Induced Breakdown Spectroscopy", Spectrochimica Acta Part B: *Atomic Spectroscopy*, 56, pp. 821–830, 2001.
Kuhn, A., et al., "Beam Quality After Propagation Nd:YAG Laser Light Through Large–Core Optical Fibers", Appl. Opt., vol. 39, No. 36, pp. 6754–6760, 2000.

(List continued on next page.)

*Primary Examiner*—Zandra V. Smith
(74) *Attorney, Agent, or Firm*—Piper Rudnick LLP; Steven B. Kelber

(57) ABSTRACT

A fiber optic laser-induced breakdown spectroscopy (LIBS) sensor, including a laser light source, a harmonic separator for directing the laser light, a dichroic mirror for reflecting the laser light, a coupling lens for coupling the laser light at an input of a multimode optical fiber, a connector for coupling the laser light from an output of the multimode optical fiber to an input of a high temperature holder, such as a holder made of stainless steel, and a detector portion for receiving emission signal and analyzing LIBS intensities. In one variation, the multimode optical fiber has silica core and silica cladding. The holder includes optical lenses for collimating and focusing the laser light in a molten alloy to produce a plasma, and for collecting and transmitting an emission signal to the multimode optical fiber.

45 Claims, 16 Drawing Sheets

OTHER PUBLICATIONS

Rai, A.K., et al., "Parametric Study of a Fiber–Optic Laser–Induced Breakdown Spectroscopy Probe for Analysis of Aluminum Alloys", Spectrochimica Acta Part B 56, pp. 2371–2383, 2001.

Rai, A.K., et al., "Laser Induced Breakdown Spectroscopy of Molten Aluminum Alloy", Applied Optics, 2002.

Multari, R.A., et al., "Effects of Sampling Geometry on Elemental Emissions in Laser–Induced Breakdown Spectroscopy", Appl. Spectrosc., vol. 50, No. 12, pp. 1483–1499, 1996.

Rai, A.K., et al., "High Temperature Fiber Optic Laser–Induced Breakdown Spectroscopy Sensor for Analysis of Molten Alloy Constituents", Review of Scientific Instrument, 2002.

Yueh, F.Y., et al., "Laser–Induced Breakdown Spectroscopy, Elemental Analysis", Encyclopedia of Analytical Chemistry, R.A. Meyers (Ed.), John Wiley & Sons, Ltd., Chichester, pp. 2065–2087, 2000.

Singh, J.P., et al., "Investigation of the Effects of Atmospheric Conditions on the Quantification of Metal Hydrides Using Laser–Induced Breakdown Spectroscopy", Appl. Spectrosc., vol. 50, No. 6 pp. 764–773, 1996.

Cremers, D.A., et al., "Spectrochemical Analysis of Liquids Using the Laser Spark", Appl. Spectrosc., vol. 38, pp. 721–729, 1984.

Majidi, V., et al., "Spectroscopic Applications of Laser–Induced Plasma", Critical Reviews in Analytical Chemistry vol. 23, No. 3, pp. 143–162, 1992.

Cremers, D.A., et al., "Remote Elemental Analysis by Laser–Induced Breakdown Spectroscopy Using a Fiber–Optic Cable", Appl. Spectrosc., vol. 49, No. 6, pp. 857–860, 1995.

Yamamoto, K.Y., et al., "Detection of Metals in the Environment Using a Portable Laser–Induced Breakdown Spectroscopy Instrument", Appl. Spectrosc., vol. 50, pp. 222–233, 1996.

TABLE 1  Concentration of elements in the Al alloys.

| Sample | Si | Fe | Cu | Mn | Cr | Ni | Zn | Mg | Al |
|---|---|---|---|---|---|---|---|---|---|
| 7075 | 0.06*<br>0.13** | .018*<br>0.15** | 1.37*<br>1.35** | 0.02*<br>0.02** | 0.20*<br>0.19** | 0.00*<br>0.00** | 5.78*<br>5.69** | 2.46*<br>2.62** | 89.86 |
| 2017 | 0.33*<br>0.30** | 0.28*<br>0.24** | 3.97*<br>3.80** | 0.45*<br>0.54** | 0.18*<br>0.02** | 0.01*<br>0.00** | 0.10*<br>0.09** | 0.73*<br>0.57** | 94.44 |
| 6061 | .65*<br>0.35** | .29*<br>0.33** | .27*<br>0.31** | 0.073*<br>0.09** | 0.073*<br>0.07** | 0.073*<br>0.00** | 0.053*<br>0.04** | 0.85*<br>0.86** | 97.95 |
| 6262 | 0.35*<br>0.37** | 0.48*<br>0.50** | 0.31*<br>0.35** | 0.01*<br>0.00** | 0.07*<br>0.06** | 0.00*<br>0.00** | 0.01*<br>0.00** | 1.00*<br>1.06** | 97.66 |
| 2024 | 0.06*<br>0.06** | 0.10*<br>0.07** | 4.33*<br>4.29** | 0.48*<br>0.59** | 0.01*<br>0.00** | 0.00*<br>0.00** | 0.05*<br>0.04** | 1.39*<br>1.45** | 93.4 |
| 2011 | 0.15*<br>0.13** | .039*<br>0.39** | 5.38*<br>5.45** | 0.02*<br>0.00** | 0.01*<br>0.00** | 0.00*<br>0.00** | 0.03*<br>0.02** | 0.09*<br>0.00** | 94.00 |
| 6063 | 0.23*<br>0.34** | 0.18*<br>0.15** | 0.06*<br>0.00** | 0.00*<br>0.00** | 0.00*<br>0.00** | 0.00*<br>0.00** | 0.00*<br>0.00** | 1.40*<br>0.48** | 99.03 |

\* Analysis based on MSU Chemical Lab (atomic absorption)

\*\* Analysis based on ICP

FIG. 9

Table 2. Analyte lines used for calibration curve

| Element | Analyte Line (nm) |
|---------|-------------------|
| Mg | 383.8258, 383.2306 |
| Cr | 359.349, 357.869, 360.533 |
| Mn | 404.136 |
| Zn | 330.2588 |
| Fe | 364.784, 383.63, 406.39, 344.061, 297.344 |
| Si | 288.158 |
| Al | 305.468 |
| Cu | 327.396 |

FIG.10

FIBER OPTIC LASER-INDUCED BREAKDOWN SPECTROSCOPY SENSOR FOR MOLTEN MATERIAL ANALYSIS

This invention was made with U.S. Government support under contract No. DE-FC26-98FT-40395 awarded by the Department of Energy. The U.S. Government may have certain rights in this invention.

BACKGROUND OF THE INVENTION

1. Field of the Invention

This invention generally relates to fiber optic spectroscopy and, more specifically, to fiber optic laser-induced breakdown spectroscopy (LIBS) sensors for molten material analysis.

2. Description of Related Art

Laser-induced breakdown spectroscopy is an advanced diagnostic technique for measuring the concentration of various elements in a test medium. This technique works for solids, liquids and gases. A pulsed laser beam is typically used to generate a spark (high temperature plasma) comprising excited neutral atoms, ions, and electrons. The laser generated plasma is allowed to equilibrate, and the emission from the neutral and ionized atoms is collected and dispersed by a spectrograph fitted with an intensified charge coupled detector. The intensity of the emission lines in the spectrum is analyzed to deduce the elemental concentrations in the sample.

In early LIBS experiments, high power laser beams were focused onto the surface of a sample using a system of lenses to generate a spark (plasma). Another assembly of lenses at a right angle to the laser beam then collected the spark light. Photomultiplier tubes with boxcar averagers, photodiode arrays with multichannel analyzers and, more recently, intensified charge coupled devices were used to record the emission signals. These LIBS experimental setups, however, are not well suited for industrial/field measurements where access to test facilities is limited and on-site alignments are difficult to complete.

Recent advances in fiber optic materials have opened up many new areas of application for the LIBS technique. Through a beam-delivery system, a laser beam may be sent to a desired location and used to perform remote measurements with an optical fiber. To generate plasma on the surface of a solid or liquid, a very high-powered laser beam is required. Thus, a difficult task in designing an optical fiber LIBS probe is coupling a high-energy laser beam into an optical fiber without damaging the fiber. Due to the breakdown threshold of the optical fiber material, optical fibers in LIBS were initially limited to delivering emission signals to the detection system. For example, a fused silica incoherent fiber bundle was used instead of a lens to collect the emission signal from the laser spark. A multiple optical fiber system, with each fiber pointing at a different region of the spark, has also been used.

Recently, more LIBS investigations using two optical fibers have been reported, one optical fiber for delivering the laser to create sparks on the surface of the sample and another optical fiber for collecting emission signals from the spark. A feature of LIBS is it can be used to perform measurements in harsh and hazardous environments, such as those in the aluminum, glass, and steel industries. Nevertheless, adjustment of the two optical fibers, one for launching the laser radiation and the other for collecting emission signals from the spark, is a very delicate and difficult task. Therefore, it is desirable to use one optical fiber both for transmitting a laser beam and for collecting emission signals from the laser-induced plasma.

U.S. Pat. No. 5,085,499 to Jeffrey, et al., discloses a method of on-site monitoring of a body of fluid stored in a tank or groundwater using an electrical spark and a fiber optic system to collect the atomic emission from the spark. This probe may be suitable for conducting materials, but may not be suitable for non-conducting materials or for studying the materials at high temperature (e.g., molten material).

U.S. Pat. No. 5,185,834 to Leslie, et al., generally discloses an optical fiber probe used with a spectrophotometer in a remote analysis system.

U.S. Pat. No. 5,798,832 to Klaus, et al., discloses a device for reducing the effects of changing sample surface by using a measuring head comprising a casing having radiation optics. The measuring head is mounted at a defined constant distance from the exit opening of the casing, so that the focal point of the laser beam is in the plane of the exit opening. The device is suitable for analyzing and compensating different surface contours or different dimensions of solid samples.

U.S. Pat. No. 5,128,882 to Cooper, et al., discloses a fiber optic cone penetrometer probe to irradiate the soil with ultraviolet (UV) or visible light to generate a fluorescence, reflection, or absorption spectrum of soil contaminates. The fluorescence spectroscopy described in this patent provides information for classifying certain molecular species, but does not form a plasma and is generally insensitive to atomic species that are important to the analysis of aluminum and steel alloy.

U.S. Pat. No. 5,379,103 to Ziger, et al., discloses a dual mode probe including separate optical fibers to conduct excitation and to collect response signals. Using separate optical fibers to conduct excitation and to collect response signals is impractical for molten materials analysis because adjustment of the two optical fibers is a very delicate and difficult task.

U.S. Pat. No. 6,147,754 to Gregory, et al., discloses a LIBS cone penetrometer in which one fiber optic carries an excitation signal from an energy source (laser), and a response signal from the sample surface is back transmitted via the same fiber. To separate the reflected excitation signal and the response signal, a decoupling mirror (a surface polished metallic mirror) was used to reflect the response signal. The mirror has a center hole of a diameter ⅛" that allows the excitation signal to pass through. Drawbacks of this device include: (1) a part of the response signal, which coincides with the excitation signal, passes through the hole in the mirror and is lost; (2) a very small focal length lens (4 mm) is used to focus the laser beam on the surface of the sample, thus allowing small variations in the sample surface to introduce inconsistency in successive measurements; (3) the probe is not suitable for high temperature analysis; and (4) the atomic emission reflecting from the decoupling mirror is focused directly on the spectrometer, limiting the probe to certain remote measurements.

Fiber optic LIBS probes have made progress in the analysis of solid and gaseous materials; however, much work remains to be done in the development of fiber optic LIBS sensors in the study of molten materials.

SUMMARY OF THE INVENTION

The present invention includes a fiber optic LIBS sensor providing on-site, online, and real-time measurement of elemental composition of molten alloy in a furnace. This sensor functions as a process monitor and control tool for the aluminum, steel, and glass industries. The sensor measures the transmission of laser energy through a multimode optical fiber. The laser radiation from the fiber is collimated and focused on an aluminum melt in the furnace, with a specially designed high temperature lens holder, such as a stainless steel lens holder, that holds the collimating and focusing lenses. Atomic emission from the plasma is collected by the same lenses and back-transmitted through the same optical fiber, and then sent to the spectrograph via an optical fiber bundle.

The fiber optic LIBS sensor further provides enhanced product quality control, saving time, and improving efficiency of the glass and metal melting processes.

The features and advantages summarized above in addition to other aspects of the present invention will become more apparent from the description, presented in conjunction with the following drawings.

BRIEF DESCRIPTION OF THE DRAWINGS

These drawings accompany the detailed description of the invention and are intended to illustrate further the invention and its advantages:

FIG. 9 is a table of experimental results for concentration of elements in Aluminum alloys, using conventional laboratory analysis techniques in accordance with an embodiment of the present invention;

FIG. 10 is a table of analyte lines used for the calibration curve for the experiments producing the results of FIGS. 5–8;

DETAILED DESCRIPTION

Figure 1:
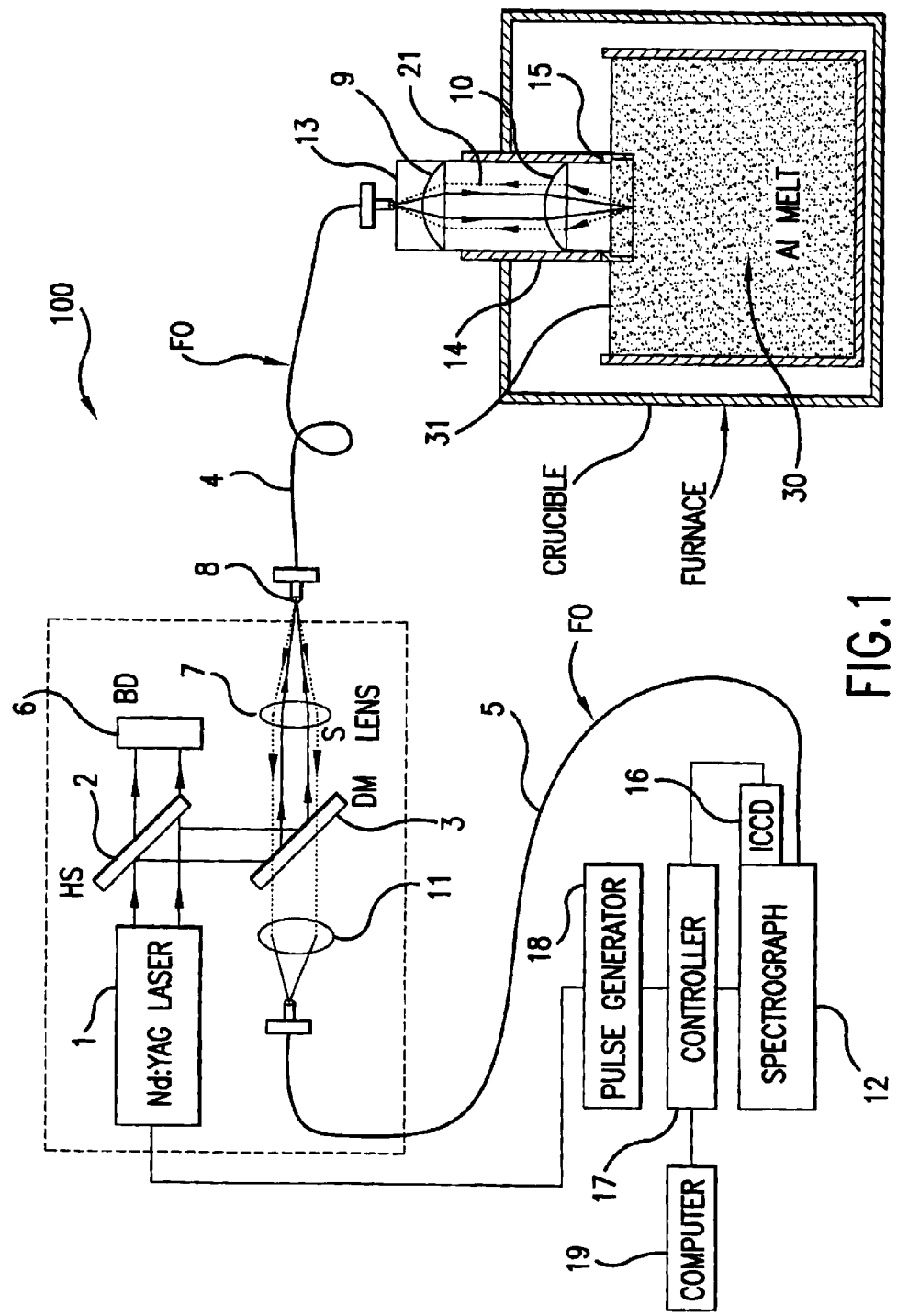
FIG. 1 is a schematic diagram of a fiber optic LIBS sensor for measuring the elemental concentration of a molten material in accordance with an embodiment of the invention.

FIG. 1 illustrates a schematic diagram of a fiber optic LIBS sensor setup for measuring the elemental concentration of a molten material in accordance with an embodiment of the invention. The fiber optic LIBS sensor 100 includes a light source 1 for providing pulsed laser; a harmonic separator 2 for directing laser light from the light source 1; a dichroic mirror 3 for reflecting the laser light from the harmonic separator 2; plano convex lens 7 for focusing the reflected laser light from the dichroic mirror 3 onto an optical fiber 4 through a cover 8; a holder 13 (also referred to herein as a "lens holder"), constructed, for example, from stainless steel, for containing collimating lens 9, which collimates the laser beam from the optical fiber 4, and focusing lens 10, which focuses the collimated beam in a melt 30 to produce plasma; and a spacer 15 for providing adjustments to the distance between the focusing lens 10 and the surface 31 of the melt 30 so as to provide precise focusing of the laser beam.

The fiber optic LIBS sensor further includes a cylindrical portion 14 such as a pipe, for holding the lens holder 13; plano convex lens 11 for focusing the collimated emission signal from the dichroic mirror 3 to the input of fiber optic bundle 5; and to a detector portion that includes a spectrometer 12 for receiving the emission signal from the fiber optic bundle 5, and transmitting information to an intensified charged couple device (ICCD) 16 (also referred to herein as a "detector"), controller 17, pulse generator 18, and processor 19, such as a personal computer (PC), minicomputer, microcomputer, or main frame computer, for analyzing the intensities of the atomic lines in the LIBS spectra of the emission signal. The elements of the fiber optic LIBS sensor are further described below.

The light source 1 may be any light source capable of generating a laser spark including but not limited to $CO_2$, excimer krypton fluoride, neodymium yttrium-aluminum garnet (Nd:YAG), ruby, titanium sapphire, aluminum gallium arsenide, indium gallium arsenide phosphide, aluminum indium gallium phosphide, and various other dye laser sources. Laser light of any wavelength, frequency and intensity may be used, so long as the light is sufficient to vaporize and excite a sample. In one preferred embodiment of the invention, the Nd:YAG laser is used as the light source.

The intensity of the laser pulse may be adjusted to be sufficient to generate a laser spark. A light source having a power density above the breakdown threshold of a test medium is typically used for LIBS measurements. Although different test media have different breakdown threshold values, laser-induced plasma is typically generated when the laser power density is over 1 $GW/cm^2$.

The frequency of the laser pulse is not particularly limited. Suitable frequencies range from 5 to 30 Hz, and preferably about 10 Hz. For example, when the sample to be analyzed is molten Al alloy, the frequency of the laser pulse is about 10 Hz. The duration of a laser pulse is generally 5–15 ns before a laser spark is generated. As a precaution, it is preferable to have a light source in the visible region. In one preferred embodiment, the Nd:YAG (1.06 mm) laser source is frequency-doubled to 532 nm by using a doubling crystal, as it is known in the art. Advantages of embodiments using frequency doubling include transforming the laser beam output to a visible (e.g., green) wavelength, thereby easing use and enhancing safety.

The harmonic separator 2 separates the frequency-doubled laser light in the light source 1 from the fundamental or main laser beam, as is known in the art. The harmonic separator 2 reflects the frequency-doubled laser light to the dicroic mirror 3 and passes the fundamental laser beam (i.e., a beam having $\lambda=1064$ nm) to a beam dump 6, which absorbs all radiation. The dichroic mirror 3 reflects the frequency-doubled laser light to the optical fiber 4 via plano convex lens 7 and transmits light from the spark via the lens 7 and optical fiber 4 to the fiber optic bundle 5. The sensor setup of the invention protects the detector 16 from potential damage caused by the laser light reflected from the sample by using the dichroic mirror 3 to reflect the laser light.

A feature of the invention is its ability to couple a high-energy laser beam to an optical fiber without damaging the fiber. The damage threshold of an optical fiber material is typically low for a pulse laser (e.g., 30 mJ/pulse for a 10 Hz, 5 nsec laser pulse). With the sensor of the invention as further described below, it is possible to transmit a pulse laser of about 20 mJ through the optical fiber without damaging the fiber. In particular, the fiber optic LIBS sensor of the present invention is designed so as to allow a sufficient amount of laser energy to be successfully delivered through the optical fiber 4 to produce a breakdown (plasma).

The optical fiber used in the sensor of one embodiment of the present invention is a silica core/silica cladding multi-mode fiber, such as the FG-1.0-UAT, available from ThorLabs, Inc., of Newton, N.J. The stability of the silica cladding allows the fiber to transmit high laser energy, and the low OH silica-core provides superior UV transmission, both of which are important in transferring the LIBS signal. The length of the fiber is about 18 m. SMA 905 stainless steel fiber connectors from ThorLabs, Inc., for example, may be used at both ends of the fiber. The fiber is preferably polished with a 0.3-mm aluminum oxide particle in the final step of fabrication. The core diameter is about 1.0 mm, and the cladding diameter is about 1.25 mm. The manufacturer's suggested maximum power capability is about 5 $GW/cm^2$. The numerical aperture of the fiber is about 0.16. The low numerical aperture provides a low beam divergence and uniform spot size that may facilitate focusing the beam after beam transmission. In one embodiment of the present invention, the Nd:YAG laser source is a CFR400, available from Big Sky Laser, Inc., of Bozeman, Mont., operating at 10 Hz and having a second harmonic ($\lambda$) of 532 nm. The pulse width (FWHM) of this example laser is about 8 ns, and the maximum pulse energy is about 180 mJ. The beam diameter is about 6.5 mm and has a Gaussian beam profile.

In the fiber optic LIBS sensor of the present invention, a spherical plano-convex fused silica lens having a 7–10 cm focal length was used to couple the laser beam into the fiber. With this lens, a 30 mJ laser beam creates a breakdown in air. This energy is the limit of the maximum laser energy that can be coupled to the optical fiber for this embodiment. A cover 8 with a 0.8 mm diameter pinhole at the center is placed just in front of the fiber to avoid damaging the boundary of the core cladding during alignment. In one embodiment, the fiber is placed about 5 mm behind the focal point in the diverging beam. With this setup, it is estimated that only about 0.6–0.7 mm of the core diameter is illuminated, and that a laser pulse of about 30 mJ pulse energy and a spot size of 0.5 mm diameter produce an energy density of about 2 $GW/cm^2$. The pulse energy is thus within the damage threshold of the fiber.

The input surface of the fiber at this laser energy level, however, may be damaged by randomly occurring hot spots in the laser profile. Thus, in accordance with one embodiment of the present invention, a 20 mJ pulse energy is used instead as the maximum input; and to reduce the solarization effect in the optical fiber for long time operation, experiments were performed at about 13.6 mJ input pulse energy.

Figure 2:
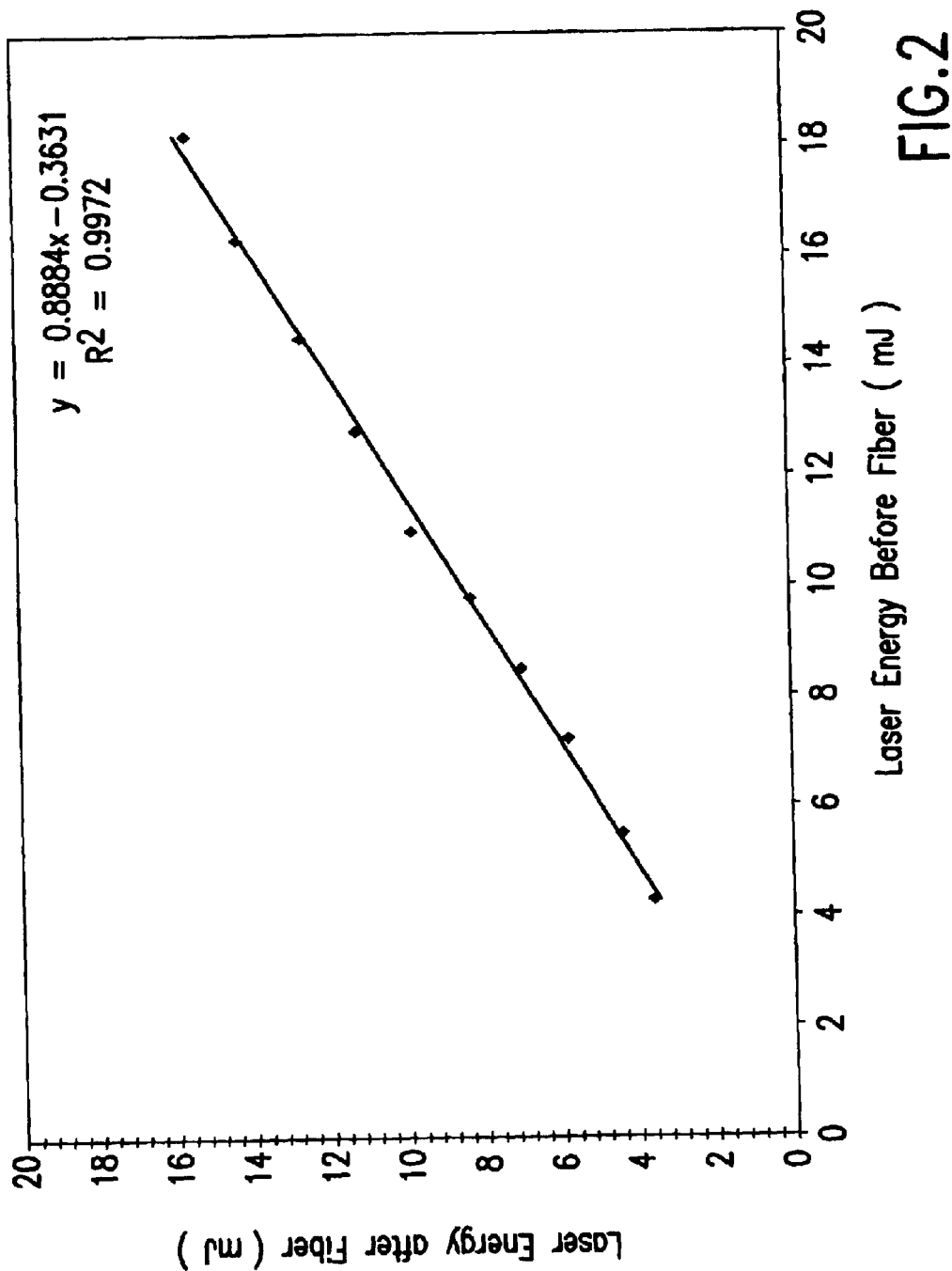
FIG. 2 is a graph illustrating the energy transmission efficiency of the optical fiber of the fiber optic LIBS sensor in accordance with an embodiment of the invention.

FIG. 2 is a graph illustrating the energy transmission efficiency of the optical fiber of the fiber optic LIBS sensor in accordance with an embodiment of the invention, which is at about 88%. That is, the laser energy exiting the optical fiber (shown in the y-axis) is about 88% of the laser energy entering the optical fiber (shown in the x-axis).

Figure 3:
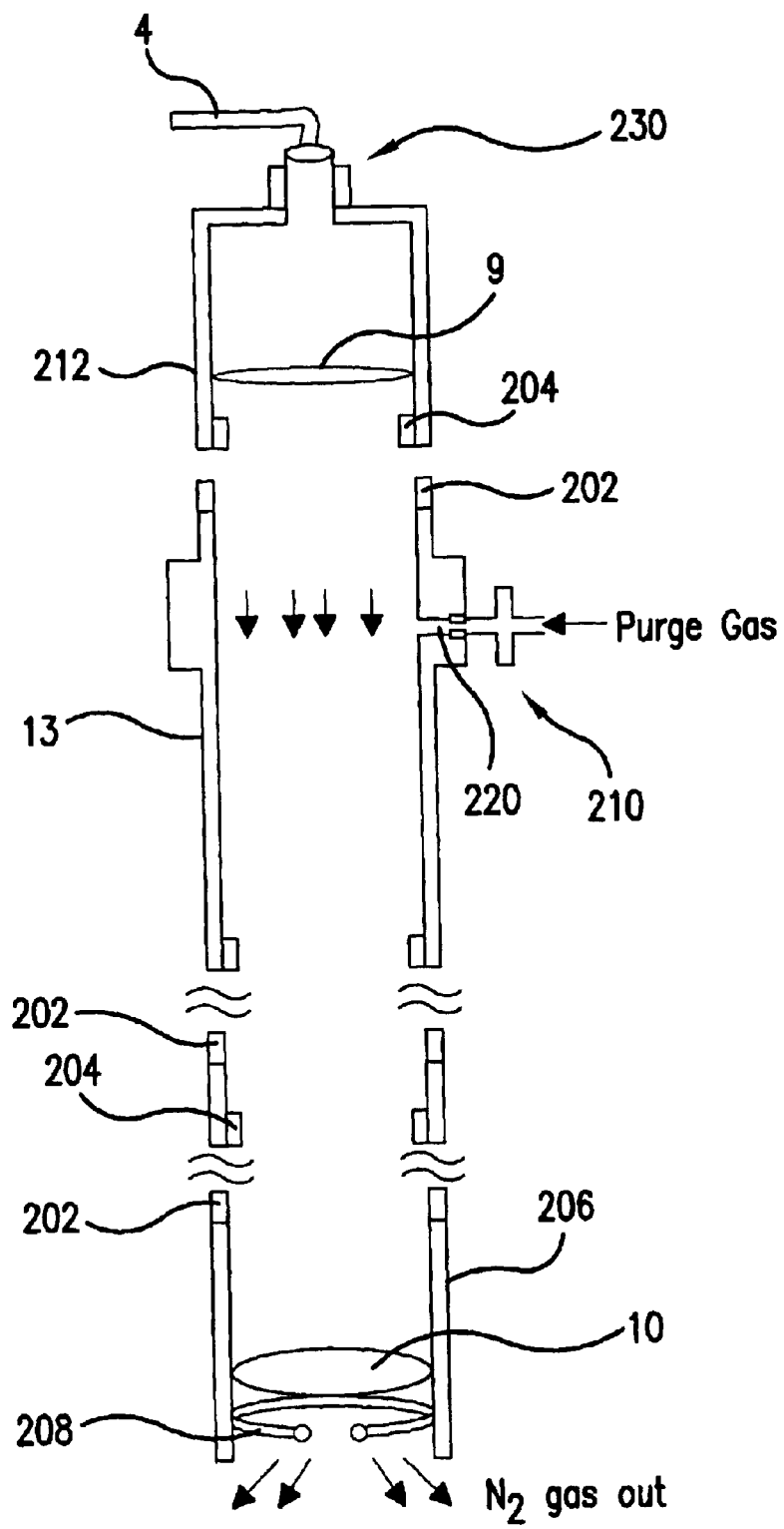
FIG. 3 is a schematic diagram of a holder housing the collimating and focusing lenses of a fiber optic LIBS sensor in accordance with an embodiment of the invention.

FIG. 3 is a schematic diagram of the holder 13, such as a stainless steel holder, housing the collimating lens 9 and the focusing lens 10 of the fiber optic LIBS sensor in accordance with an embodiment of the invention. The holder 13 plays an important role in producing plasma in the melt and collecting emission signals from the plasma. Collimating lens 9 collimates the laser beam from the optical fiber 4, and focusing lens 10 focuses the collimated beam from the collimating lens 9 in a molten alloy to produce plasma. The holder 13, in accordance with one embodiment of the present invention, is assembled from, for example, six different 1-foot stainless steel tubes. The 1-foot stainless steel tubes, each having an inner and an outer diameter of 0.8685" and 1.2265", respectively, are connected to each other by male 202 and female 204 fine threads.

A bottom piece 206 of holder 13 is provided to house the focusing lens 10. A recess is cut in an inner wall at a bottom end to house an internal snap ring 208. The snap ring 208 prevents movement of the focusing lens 10. In an embodiment of the present invention, six passages are provided in the inner wall beside the lens 10 and snap ring 208 for an outlet flow of nitrogen gas ($N_2$), which enters through an upper piece 220 of the holder 13. The flow of nitrogen gas through the passages helps to keep the lens 10 and snap ring 208 cool and prevents the aluminum melt from reaching the surface of the lens 10. A valve 210, such as a valve manufactured by Swagelok of Solon, Ohio, is provided at a top portion of holder 13 to allow adjustment of an inlet flow of nitrogen gas.

In an embodiment of the present invention, an aluminum or other material flange with an outer diameter of 6" and an inner diameter of 1.23" supports the holder 13 with pipes made, for example, from stainless steel. Insertion of a thermocouple in the aluminum flange is made possible so as to allow measurements of temperatures at the bottom end of the holder 13. A flowmeter, connected, for example, via valve 210, is provided to control the inlet flow of $N_2$. The outlet and inlet flows are adjusted so as to maintain the melt surface at the focal plane of the focusing lens 10. In an embodiment of the invention, the outlet flow is kept as large as possible to cool the whole lens holder 13.

At the top of the holder is a holder top 212, comprised, for example, of aluminum, containing collimating lens 9, the holder top 212 having inner and outer diameters that are the same as the tubes of holder 13, the holder top 212 and the holder 13 being connected via, for example, male and female threads 202, 204. The holder top 212 houses the collimating lens 9 via, for example, a spiral lock ring. A mechanism 230 is provided at one end of the holder top 212 to connect the optical fiber bundle 4 and the stainless steel fiber connector for the optical fiber 4.

The holder top 212 further includes a rotating ring, which provides fine adjustment of the distance between an output of the optical fiber 4 and the collimating lens. With the assistance of this fine adjustment, the laser beam may be collimated through the cylindrical portion 14 without losing any part of the circular spot of the laser beam. That is, the distance between the output end of the optical fiber 4 and the collimating lens 9 may be adjusted so that the collimating beam illuminates the focusing lens 10 without losing any portion of the laser beam. Test results with a holder 13 comprised of stainless steel have shown that the alignment of the beam remains undisturbed even after the holder 13 has bean in the furnace for several hours. The test results demonstrate that the holder 13 remains straight in the furnace (at high temperatures) and can be used to focus the laser radiation on the surface of the molten alloy and collect plasma emission with minimal loss.

Focusing the laser light at the periphery of the bottom end of the probe is a very sensitive task since this is a very delicate part of the sensor. The invention achieves this very sensitive task by introducing a spacer 15, as shown in FIG. 1, below the lens holder 13. The spacer 15 is made, for example, from a stainless steel piece having inner diameter equal to the outer diameter of the lens holder 13. In one embodiment, the spacer 15 has a loose female thread that fits into a male thread at the bottom end of the lens holder 13. With these male-female threads, it is possible to adjust the distance between the focusing lens 10 and the melt surface, and to focus the laser light on a desired location to obtain strong LIBS spectra. In addition to the precise focusing of laser light on the surface of the melt, the spacer 15 helps to maintain the lens holder 13 in the middle of the cylindrical portion 14, which help in collecting all of the emission signal 21.

In an embodiment of the present invention, the collimating lens 9 and focusing lens 10 collect the emission signal 21 and transmit the emission signal 21 in the reverse direction through the same optical fiber 4 that transmitted the laser light. After passing the lens 7, the collimated emission is separated from the laser light through the dichroic mirror 3 and is focused onto the fiber optic bundle 5 by, for example, a 20 cm focal length lens 11. The fiber optic bundle 5, in one embodiment of the present invention, comprises 78 fibers, each with a 10 $\mu m$ diameter and a 0.16 numerical aperture. Ends of the fiber optic bundle 5 are round-to-slit types. The slit-type ends of the fiber optic bundle 5 then deliver the emission signal 21 to the entrance slit of the 0.5 m spectrometer 12, such as Model HR 460 from JOBIN YVON-SPEX of Edison, N.J., which is equipped with a 2400 line/mm grating blazed at 300 nm. An intensified charged couple device ICCD 16 (e.g., Model ITE/CCD from Princeton Instruments of Trenton, N.J.), for example, may be used as a detector with controller 17 (e.g., Model ST 133 from Princeton Instruments). A programmable pulse delay generator 18 (e.g, Model PG-200 from Princeton Instruments) connected to the controller 17 may be used to gate ICCD 16. A processor 19, such as a Dell Dimension M 200a computer, is connected to controller 17 and operates software, such as WinSpec/32 software available from Princeton Instruments. Processor 19 is used for data acquisition and analysis. To obtain good signal-to-noise data, a typical sample time is 10 seconds, which corresponds to an average of 100 laser pulses. The intensities of the atomic lines observed in the LIBS spectra are integrated and used in LIBS analysis.

The invention is further explained below with reference to examples that are provided for illustration purposes only and are not intended to be limiting.

Figure 4:
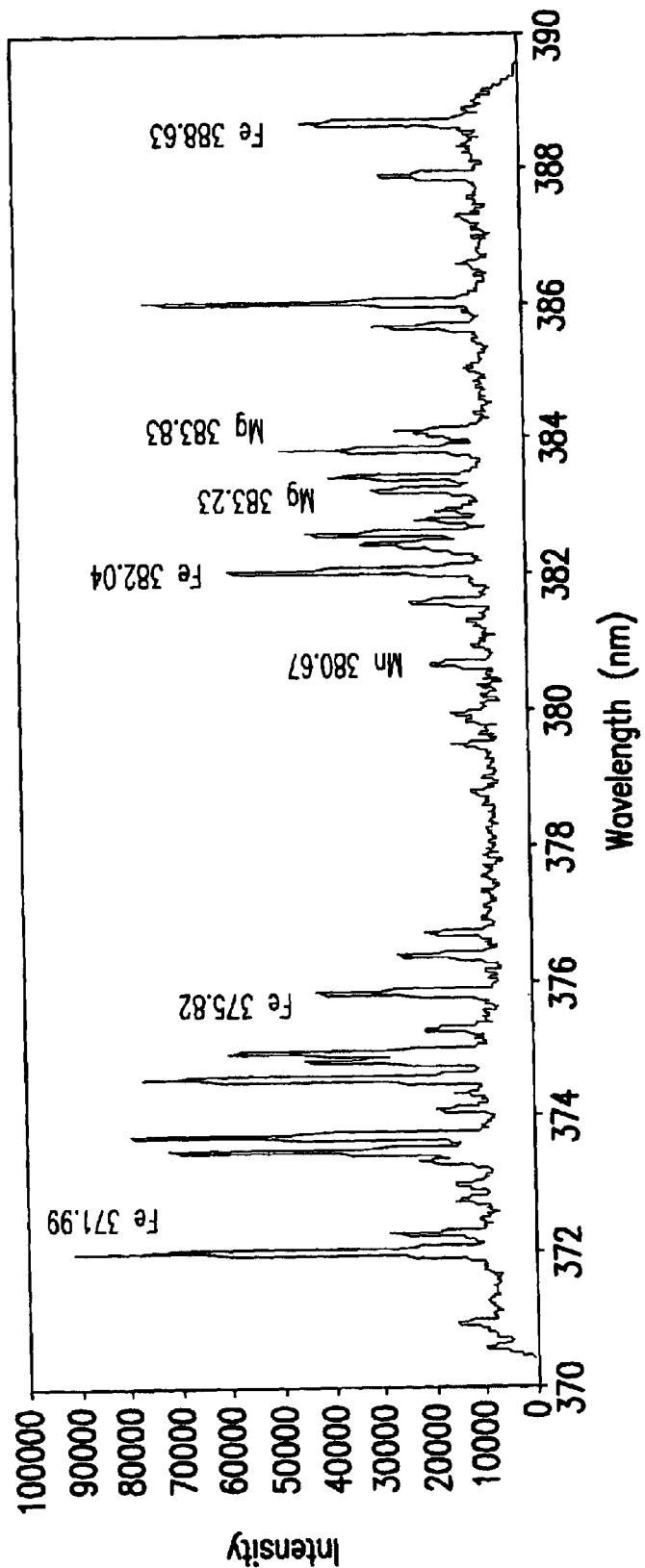
FIG. 4 is a graph illustrating the LIBS spectra of solid Al recorded using a fiber optic probe.
Figure 5:
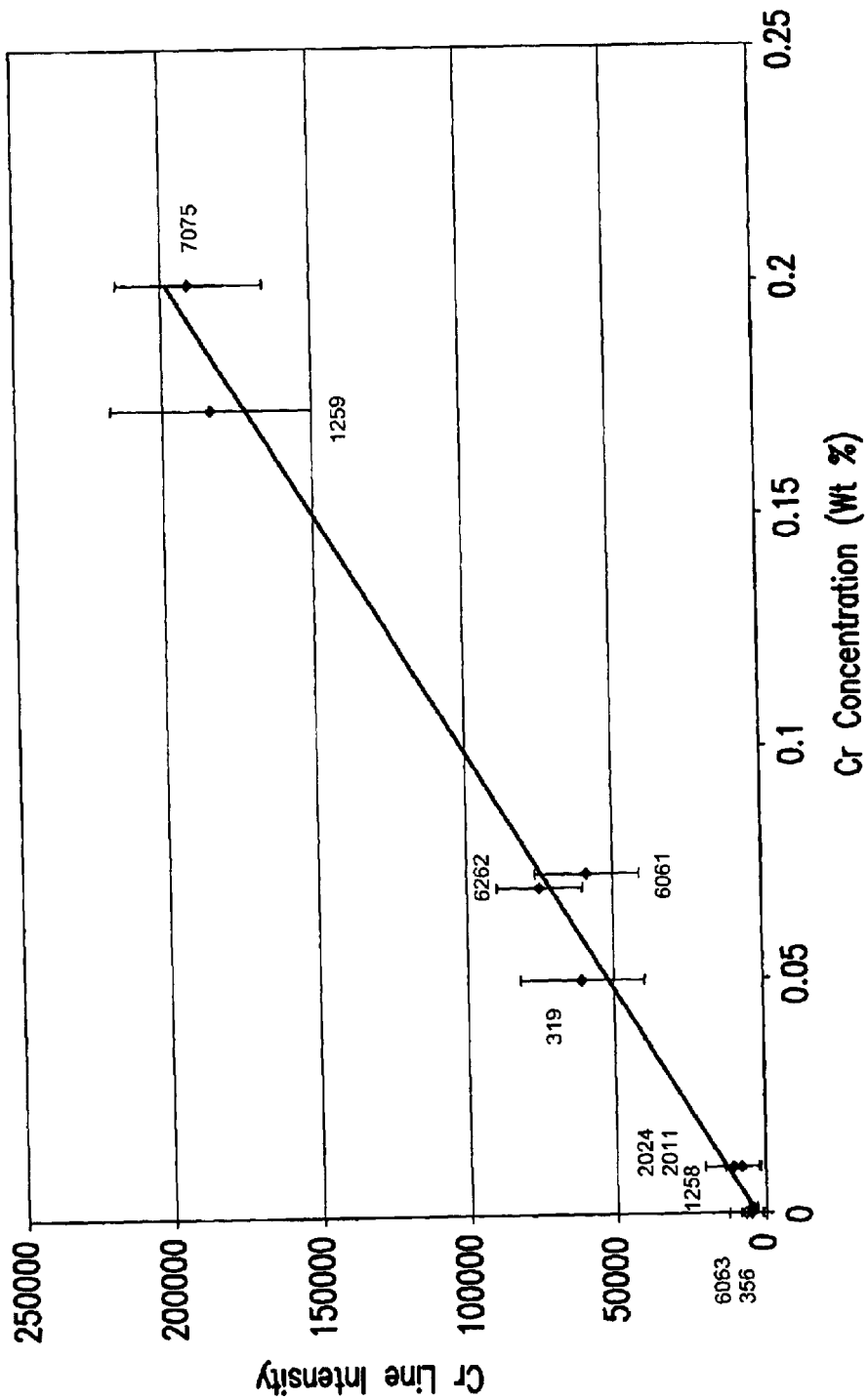
FIG. 5 is a graph illustrating a calibration curve for Cr based on its absolute line intensity in the LIBS spectra of solid Al alloy.
Figure 6:
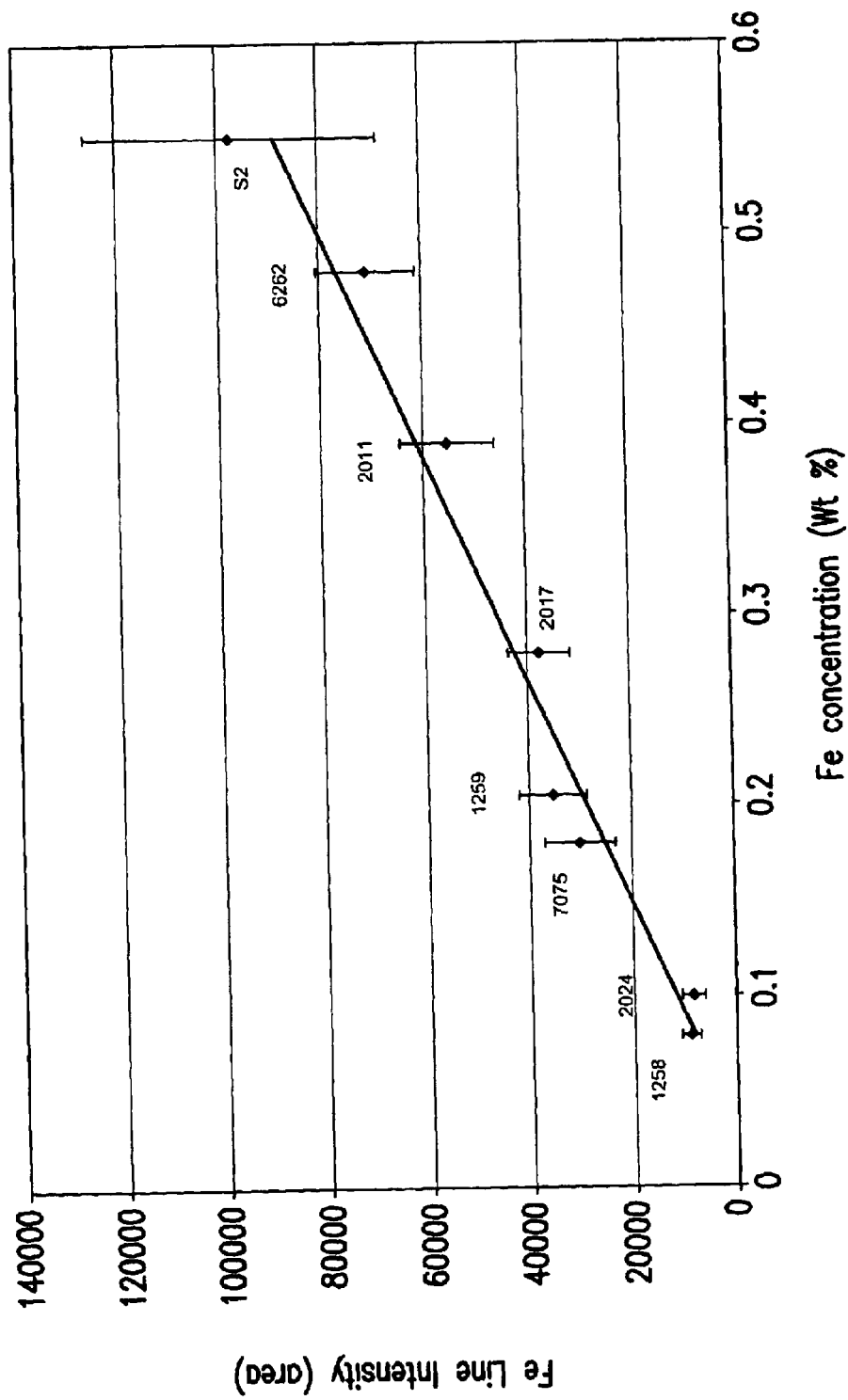
FIG. 6 is a graph illustrating a calibration curve for Fe based on its absolute line intensity in the LIBS spectra of solid Al alloy.
Figure 7:
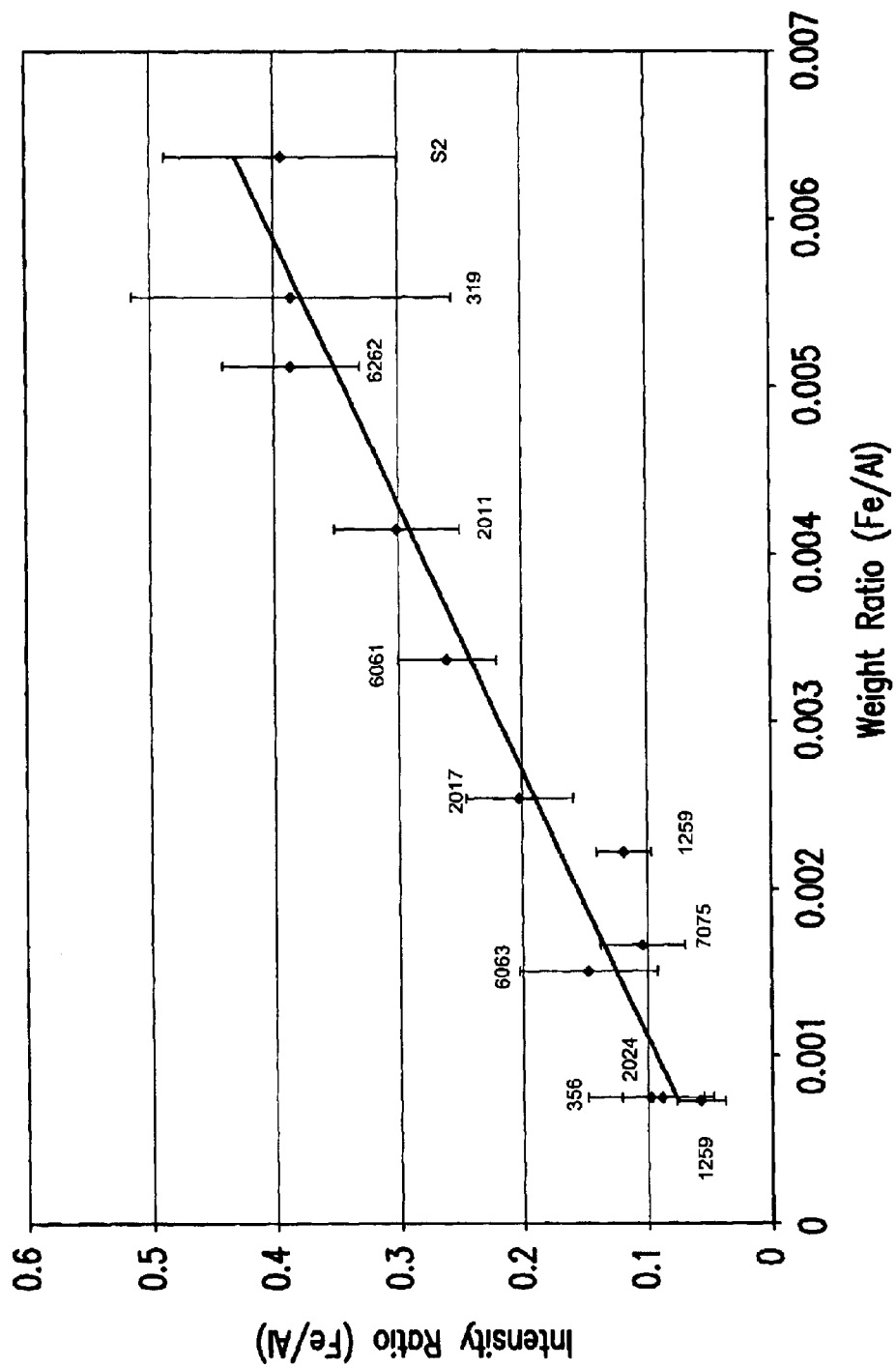
FIG. 7 is a graph illustrating a calibration curve for Fe using the ratio of an analyte line Fe with an Al reference line in the LIBS spectra of solid Al alloy.

To evaluate the performance of the fiber optic LIBS sensor of the invention, a solid aluminum (Al) alloy was tested using several experimental variables, including laser energy, gate delay and width, detector gain, lenses with different focal lengths, and sample surfaces. In order to provide high reliability and repeatability in the analysis, measurements of plasma parameters, such as electron density and plasma temperature, were also taken to determine their influence on the measurement results. The performance of the fiber optic LIBS sensor was also compared with that of a LIBS sensor that does not use an optical fiber to transmit the laser beam. FIG. 4 is a graph illustrating the LIBS spectra of solid Al recorded at 2 $\mu s$ gate delay and width using a fiber optic probe in accordance with an embodiment of the invention. The LIBS spectra of more than ten different Al alloy samples were recorded to obtain calibration data, and linear calibration data for numerous elements such as Chromium (Cr), Zinc (Zn), Iron (Fe), Nickle (Ni), Manganese (Mn), Magnesium (Mg), and Copper (Cu) were obtained. FIGS. 5 and 6 are graphs illustrating calibration data for Cr and Fe, respectively, based on their absolute line intensities in the LIBS spectra of solid Al alloy. FIG. 7 is a graph illustrating a linear calibration curve for Fe using the ratio of an analyte line Fe with an Al reference line in the LIBS spectra of solid Al alloy.

After measuring the concentration of the minor elements of the solid Al alloy, the fiber optic LIBS sensor was tested on a molten alloy by recording the LIBS spectra of seven different samples in the molten phase. Calibration curves were obtained for Cr, Mg, Zn, Cu, Silicon (Si); etc., for the quantitative analysis of these elements in molten alloy. The melt was produced in a laboratory furnace, such as model L-83102-56622 available from GS, LINDBERG of Asheville, N.C. The test aluminum sample was placed in a crucible, such as an AC 36265 $Al_2O_3$ crucible available from Ozark Technical Ceramics, Inc., of Webb City, Mo. The LIBS spectra of seven molten alloys were observed and recorded without damage to the focusing lens by the adhered Al melt. It was also observed that the flow of purging gas was kept a little high. The inlet flow rate of the purging gas was about 1.5–3.0 l/min., and the outlet flow rate of the purging gas was about 100–600 ml/min. This provides a relatively constant LIBS signal over time. At times, it was observed that the signal strength decreased, but then it regained after the flow rate of the purging gas was adjusted.

Figure 8:
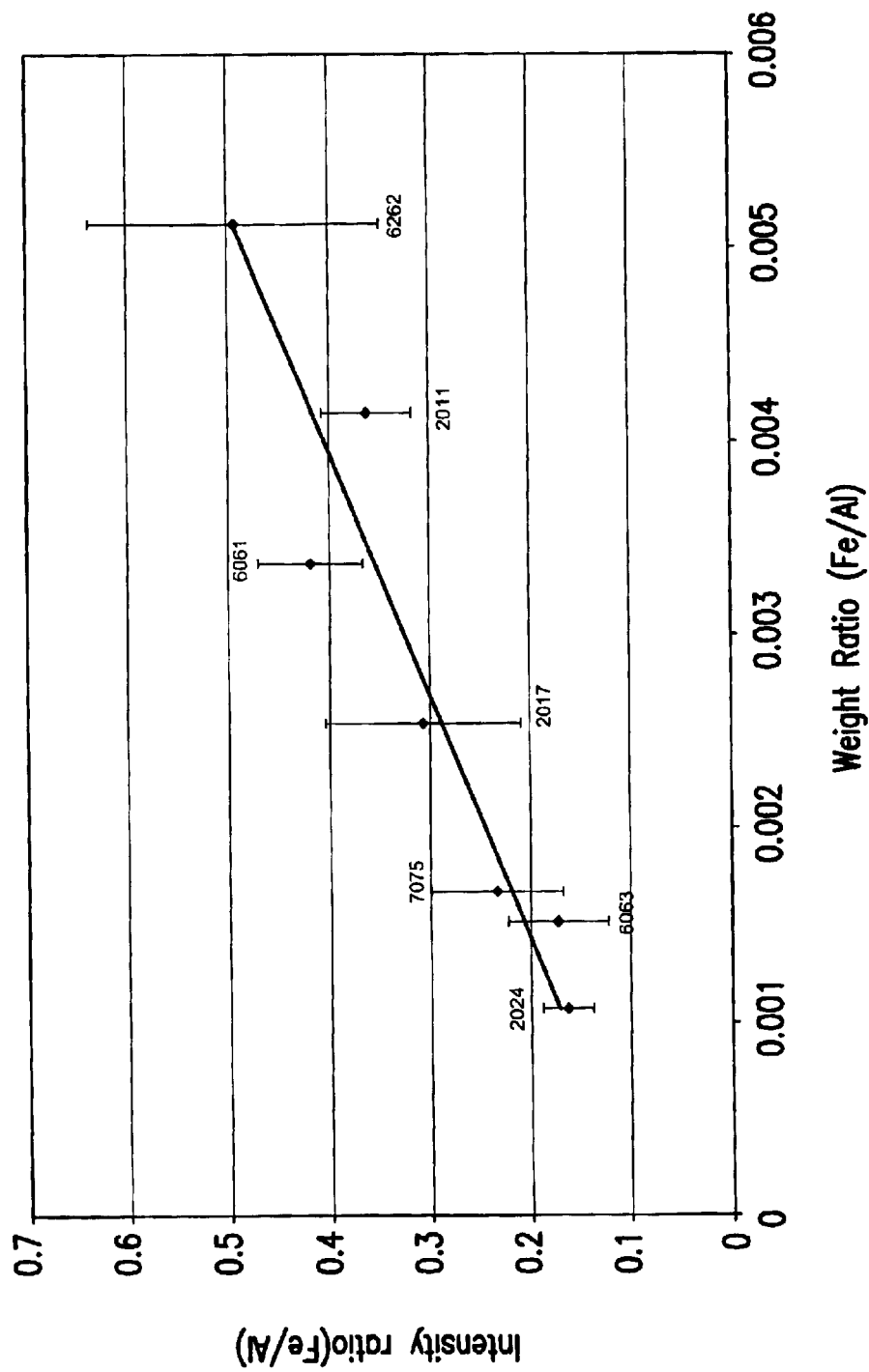
FIG. 8 is a graph illustrating a calibration curve for Fe using the ratio of an analyte line Fe with an Al reference in the LIBS spectra of molten Al alloy.

FIG. 8 is a graph illustrating a calibration curve for Fe using the ratio of an analyte line Fe with an Al reference line in the LIBS spectra of molten Al alloy. In a sample melt experiment conducted in accordance with an embodiment of the present invention, the LIBS signal was so high that it was recorded at a very low laser power (9.5 mJ). The LIBS spectra was also recorded by inserting the probe at different depths inside the melt. It was determined that when the depth is increased, a higher inlet flow rate must be used in order to obtain a good LIBS signal. This is consistent with the predictions that, when the depth is increased, the melt Al tries to enter the probe and push it to its original position (the focal plane), so that a higher inlet flow rate is necessary. This indicates that the probe was working properly.

Table 1, shown in FIG. 9, presents the composition of the seven different alloy samples that were recorded in the above condition. The intensity of the atomic lines observed in the LIBS spectra were integrated and used in the LIBS analysis. Table 2, shown in FIG. 10, contains the analyte lines of Cu, Cr, Mn, Mg, Fe, Al, Zn and Ni that were used to obtain the calibration curve.

Figure 11:
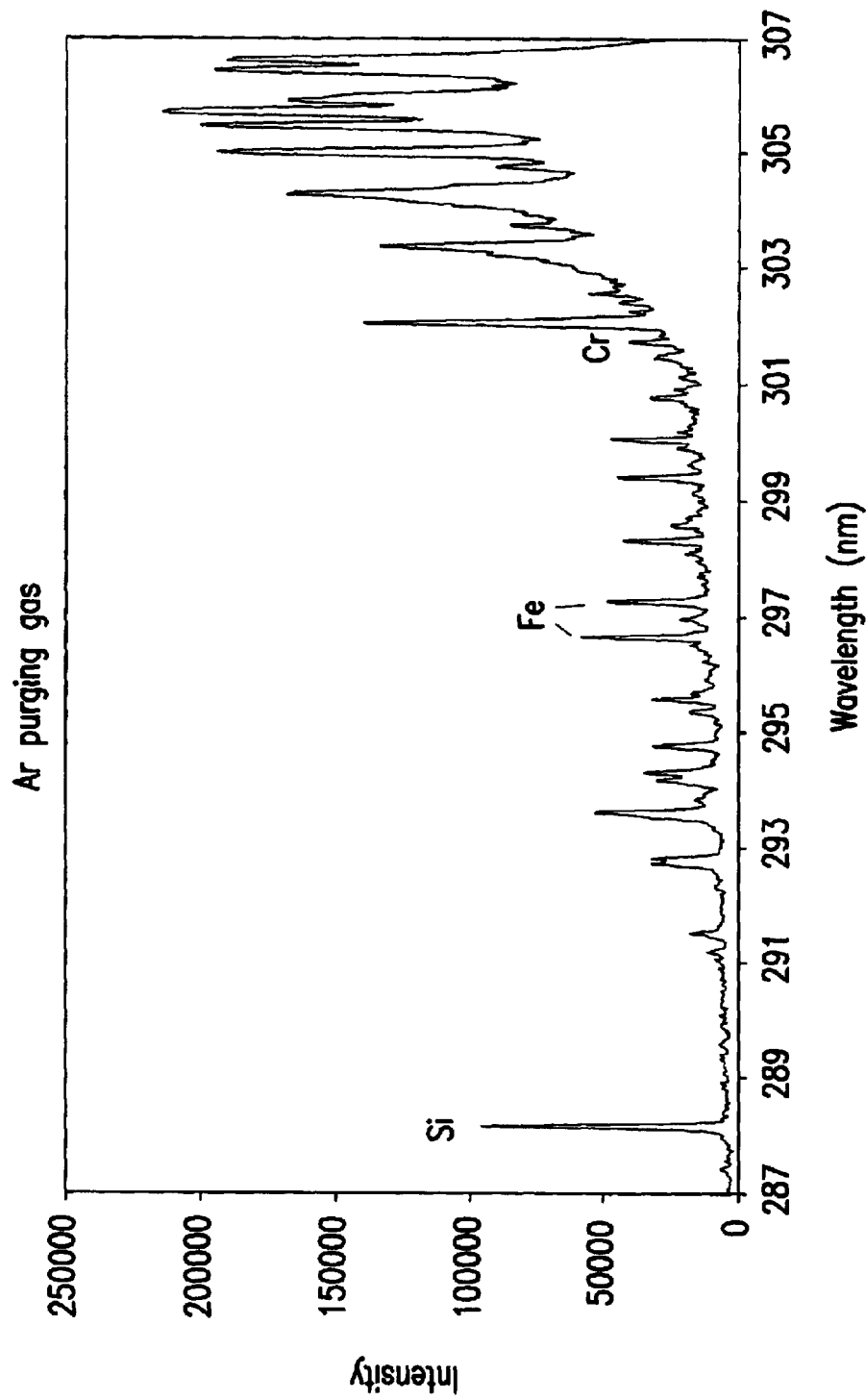
FIGS. 11 and 12 are graphs illustrating the LIBS spectra taken with Argon (Ar) and Nitrogen ($N_2$) purging gases, respectively.
Figure 12:
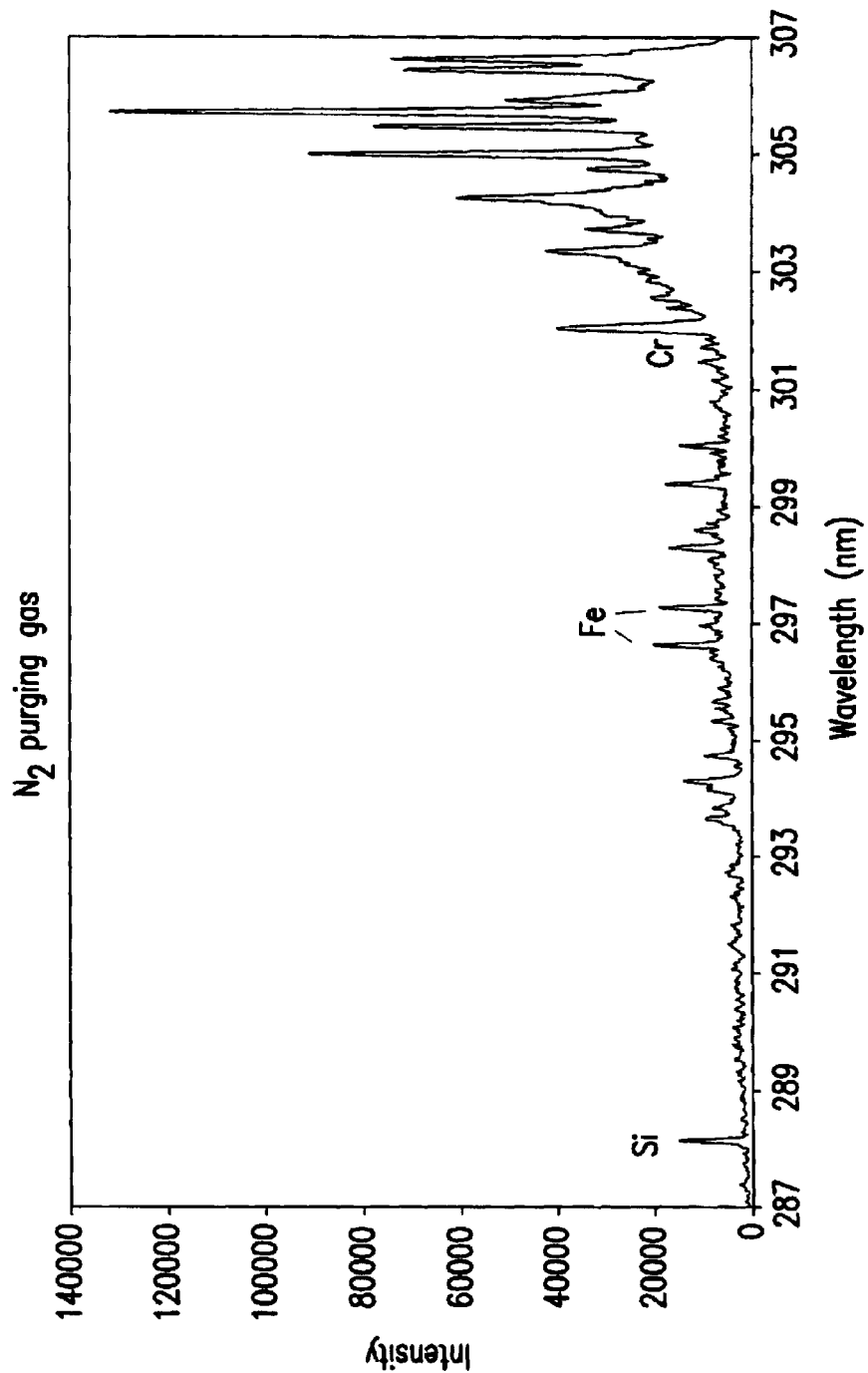

The effects of different purging gases on the LIBS signal were also investigated in the experiment. For example, it was determined that the LIBS signal was very weak in the presence of He as a purging gas, even undetectable. The Ar gas, on the other hand, enhanced the LIBS signal much more effectively than did the He or $N_2$ gas. FIGS. 11 and 12 contain graphs that illustrate that, under the same experimental conditions (laser power, inlet, outlet gas flow and depth), the intensity of Si at wavelength 288.158 nm was about five times higher in the Ar gas, as shown in FIG. 11, than in the $N_2$ gas, as shown in FIG. 12.

After testing the sensor in the laboratory furnace, the probe was tested in the industry to explore the possibility of using this probe in an actual furnace in the factory. In testing the fiber optic LIBS probe in the industrial environment, it was determined that it is not possible to insert the probe from the top (perpendicular to the melt surface) of the furnace. However, the probe can be easily inserted at an angle (preferably 45°) into the furnace from the furnace wall. An experiment was performed to determine the effect of the angle of incidence of the laser light on the sample surface by measuring the intensities of analyte emissions. The LIBS signal, using a probe in accordance with embodiments of the present invention, was recorded for 0°, 15°, 30°, 45° and 60° angles of incidence. The sample was rotated from 0° (normal incidence of the laser beam on the sample surface) to 60° in 15° steps. Great care was taken to maintain constant lens-to-sample distance during each rotation of the angle. For this experiment, the axis of rotation of the sample was adjusted so as to coincide to the axis of the incident beam. The experiment was performed using lenses of different focal lengths to focus the laser radiation on the sample. The results are as follows.

Figure 13:
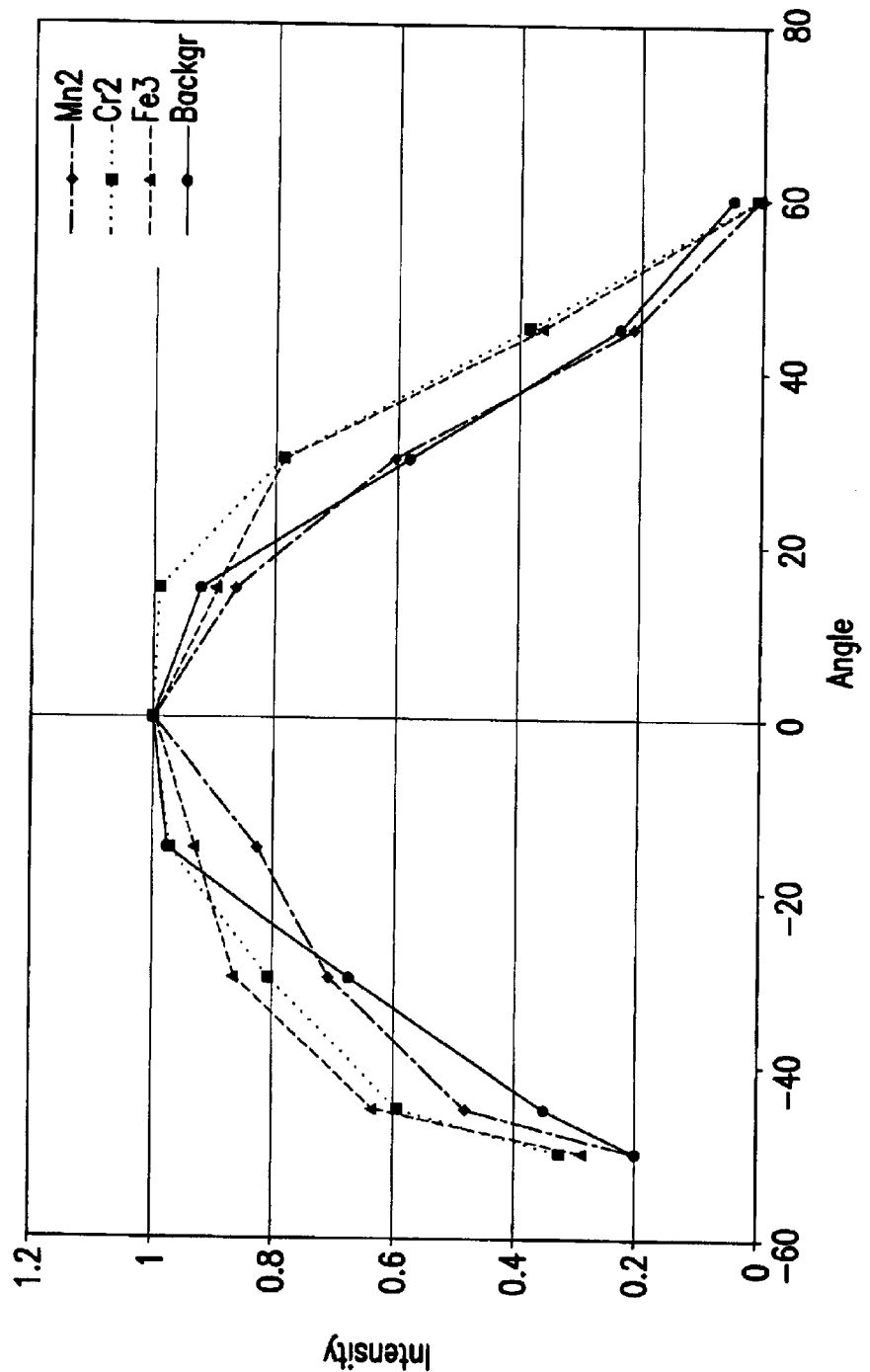
FIG. 13 is a graph illustrating variation of line intensity with angle of incidence in the LIBS spectra of solid Al alloy recorded at 0.5 $\mu$s gate delay using a 5 cm focal length lens.
Figure 14:
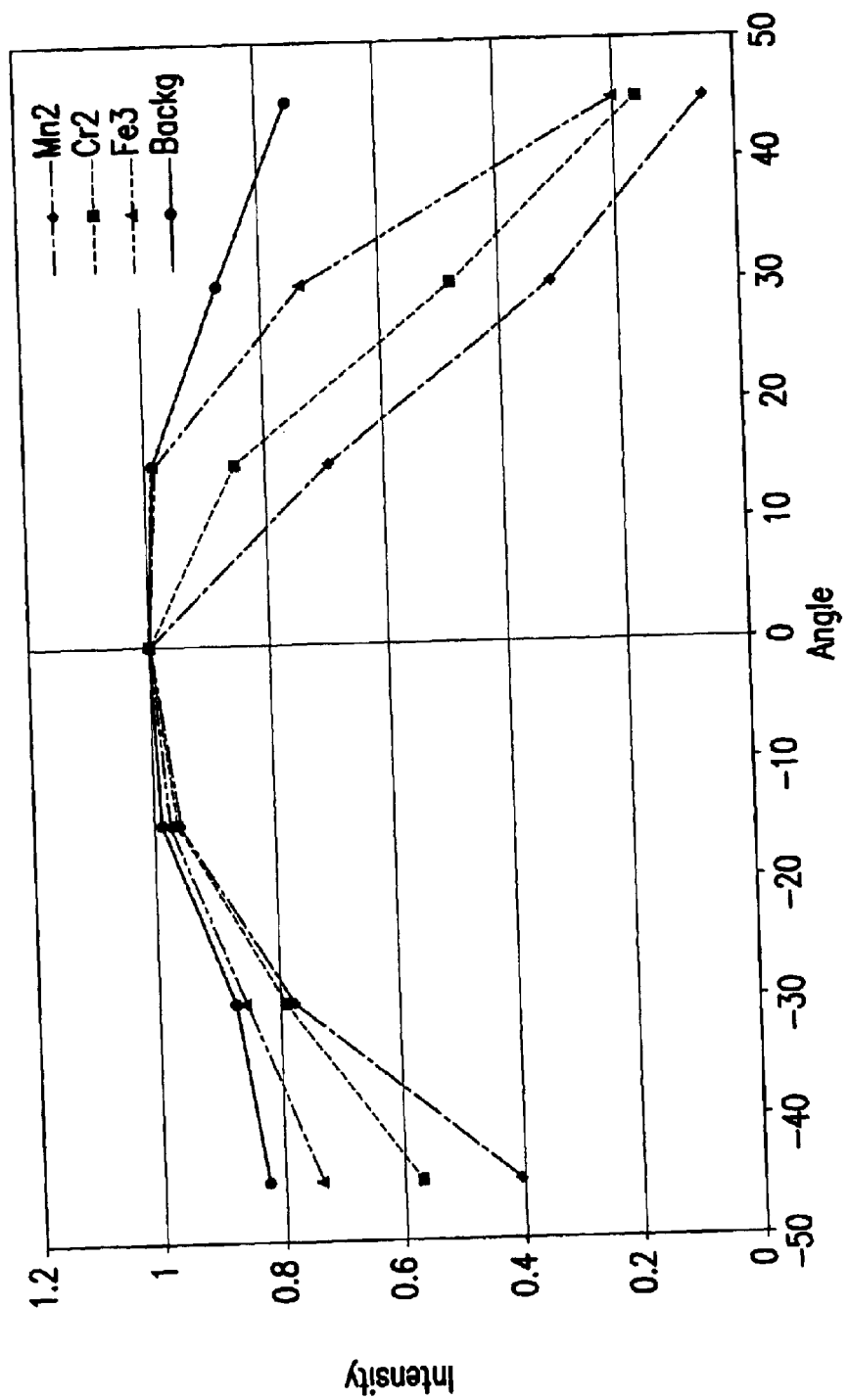
FIG. 14 is a graph illustrating variation of line intensity with angle of incidence in the LIBS spectra of solid Al alloy recorded at 2 $\mu$s gate delay using a 5 cm focal length lens.

Lens with Focal Length of 2". The LIBS spectra of neutral lines (Fe, Cr, Mn, etc.) and ion lines at different angles of incidence between 0° and 60° were recorded for different gate delays of 0.3, 0.5, 1, 2 and 3 $\mu s$. The results show that both the line intensity and the background continuum decreased when the angle of incidence changed from 0° (normal incidence) to 60°. FIGS. 13 and 14 are graphs illustrating variations of line intensity and background continuum at different angles of incidence on a sample surface in the LIBS spectra of solid Al alloy recorded at 0.5 $\mu s$ and 2 $\mu s$ gate delays, respectively. FIGS. 13 and 14 illustrate that in the case of a neutral line, the decrease in intensity was steeper at a higher delay, but in the case of a background continuum, the trend was the opposite. This occurred because, in the first several microseconds after the laser pulse, the background continuum was strong, but decreased rapidly with gate delay time, whereas the line intensity appeared strong for several microseconds after the laser pulse. Therefore, the decrease in line intensity is steeper at a higher delay. A similar type of experiment was performed by Multari, et al., "Effect of Sampling Geometry on Elemental Emissions in Laser-Induced Breakdown Spectroscopy," 50 Journal Applied Spectroscopy, 1483–1499 (1996), who noticed that the emission intensities were maximum at 0° and decreased as the sample was rotated to 40°; and beyond 40°, emission intensity increased. The increases were greatest for the neutral emission, which almost reached the intensity observed at a normal incidence as the sample was rotated to 60°. Contrary to the observation of Multari, et al., the observed intensity of the neutral emission, ionized species and background continuum still decreased beyond 40° and became minimum at 60° in the experiments in accordance with the present invention. In these experiments, the intensities of neutral emission, ionized species, and background continuum were at a maximum only at 0°.

As the sample was rotated, the mass of ablated material and the temperature of the atomic material ejected from the surface may have changed, accounting for the observed changes in emission intensities. Multari, et al., further disclosed that no variation in the mass of ablated material was observed as the sample was rotated from 0° to 60°, eliminating changes in total ablated mass as the cause of the observed decrease in emission intensity. The experiments of the invention show a monotonic decrease in plasma temperature as the sample rotates from 0° to 60° (i.e., a decrease in intensity of the neutral lines as well as the ionized species). Furthermore, collection of the atomic emission decreased as the sample rotated from 0° to 60°, resulting in a net decrease in intensity of the atomic lines. Another reason for the decrease in the LIBS signal is the coupling of laser energy with the sample surface. The amount of reflection of laser light from the sample surface changes at different angles of rotation. During the experiments in accordance with embodiments of the present invention, it was noticed that the amount of reflection from the sample surface increased with an increase in the angle of rotation, which ultimately reduced the laser energy and the plasma/atomic emission, resulting in a net decrease in the intensity of the LIBS signal.

Figure 15:
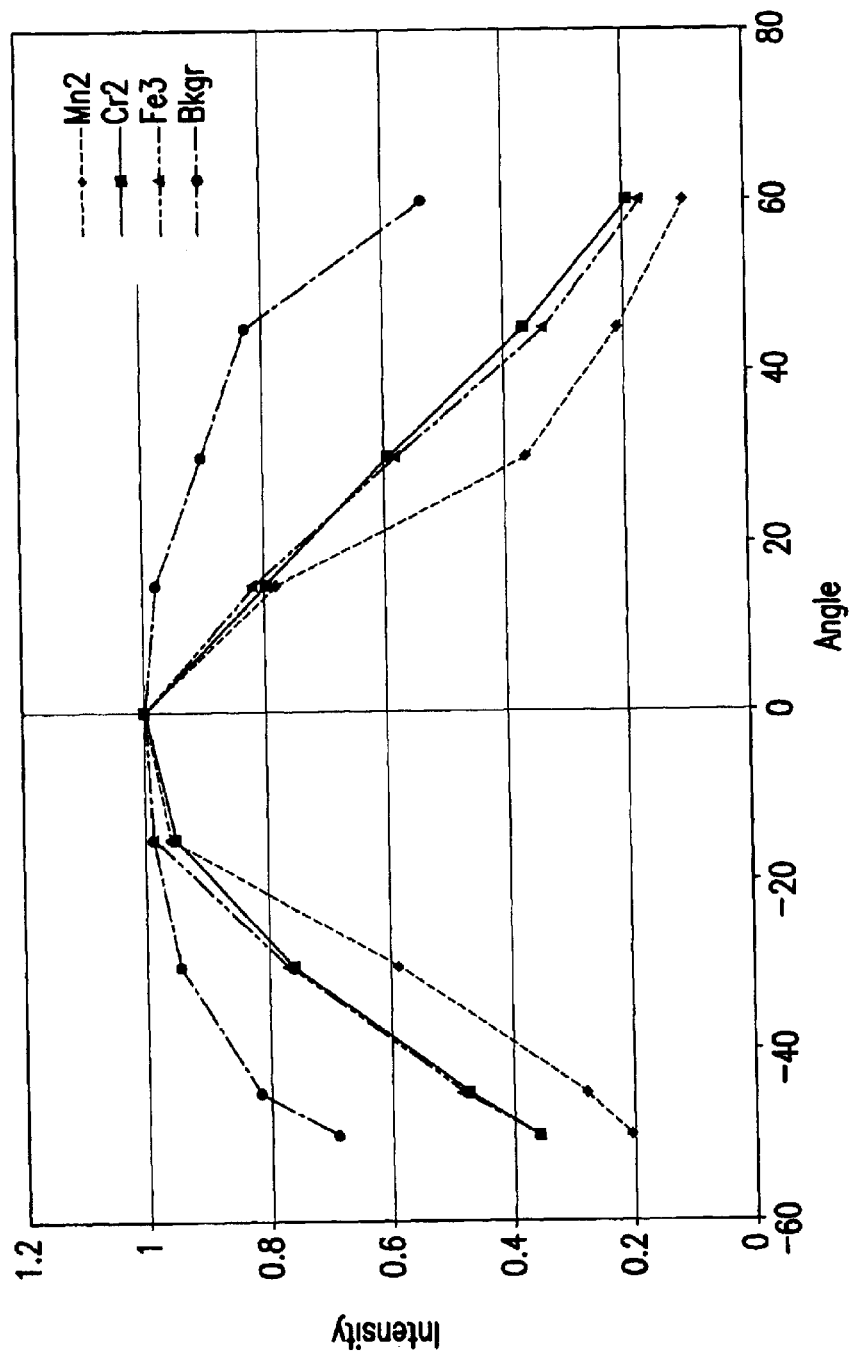
FIGS. 15 and 16 are graphs illustrating variation of line intensity with angle of incidence in the LIBS spectra of solid Al alloy recorded at 0.5 $\mu$s and 2 $\mu$s gate delay, respectively, using a 10 cm focal length lens.
Figure 16:
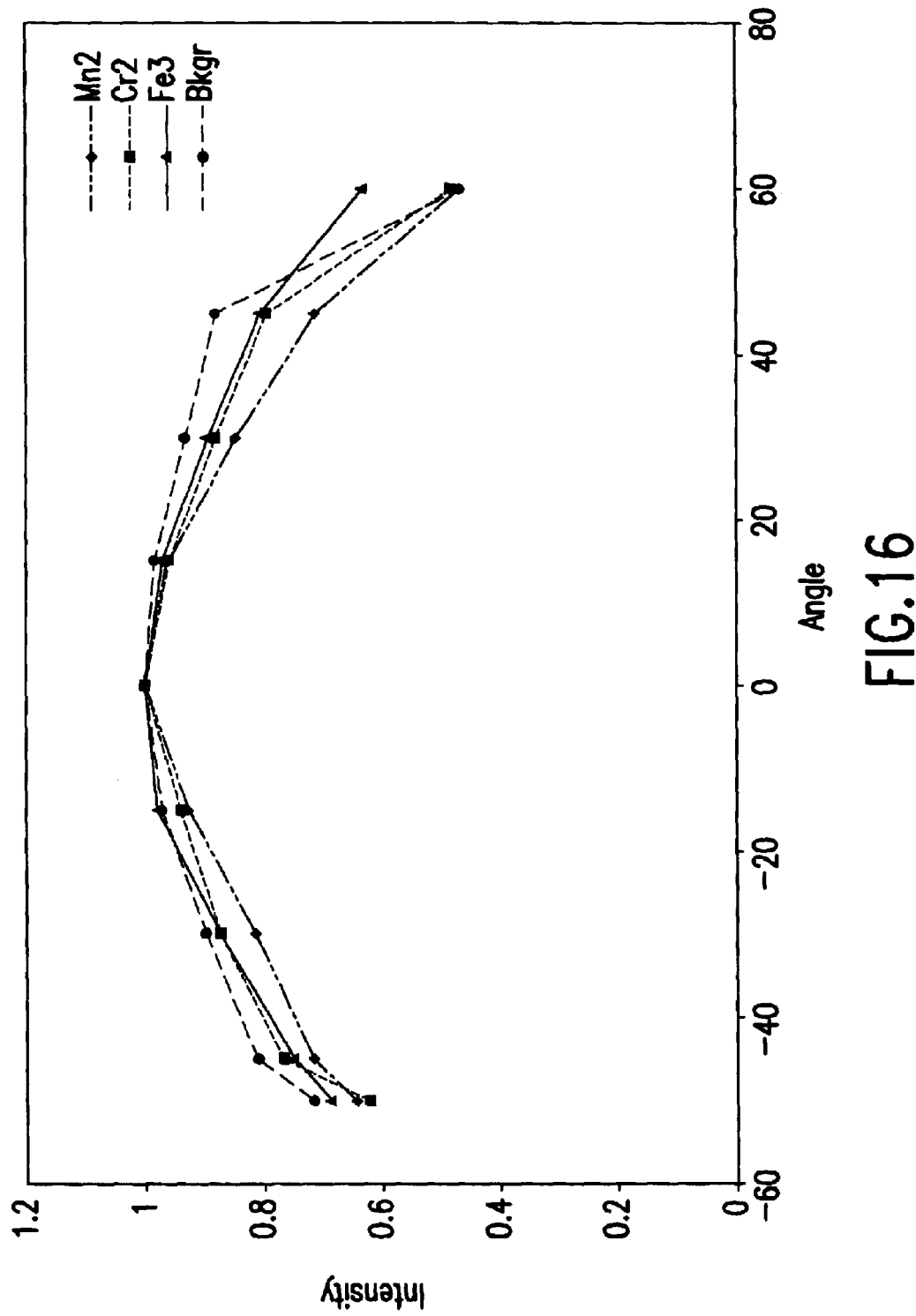

Lens with Focal Length of 4". In this experimental setup, the general LIBS signal was found to decrease as the rotation angle of the sample increases, but the trend for atomic emission is opposite that of the lens having a focal length of 2". That is, the decrease in the atomic intensity line is steeper with a lower delay (0.5 $\mu s$), as illustrated in FIG. 15, than it is with a higher delay (2 $\mu s$), as illustrated in FIG. 16. The dependence of the rotation angle on the intensity of the background continuum is similar to that of a lens having a focal length of 2". This experiment setup further demonstrates that the effect of the angle of incidence of the laser light on the sample surface is smaller when the laser beam is focused using a lens with a longer focal length.

Example embodiments of the present invention have now been described in accordance with the above advantages. It will be appreciated that these examples are merely illustrative of the invention. Many variations and modifications will be apparent to those skilled in the art.

What is claimed is:

1. A laser-induced breakdown spectroscopy probe for producing plasma in a molten alloy and collecting emission from the plasma, the probe comprising:
    a collimating lens to collimate a laser beam;
    a focusing lens to focus the collimated beam on the molten alloy to produce the plasma; and
    a holder for containing the collimating lens and the focusing lens;
    wherein the holder includes a gas valve to adjust the amount of inlet flow of a gas in the holder.

2. The probe of claim 1, wherein the holder further comprises a plurality of tubes.

3. The probe of claim 2, wherein the tubes comprise stainless steel.

4. The probe of claim 2, wherein the tubes are connected to each other by male and female threads.

5. The probe of claim 1, wherein the holder includes a bottom piece for housing the focusing lens.

6. The probe of claim 1, wherein the holder includes an internal snap ring to prevent movement of the focusing lens.

7. The probe of claim 6, wherein the holder includes an upper portion, wherein the gas enters the holder via the upper portion, and wherein the tubes include passages that provide an outlet flow of nitrogen gas.

8. The probe of claim 7, wherein the flow of the gas through the passages cools the focusing lens and the snap ring and prevents the molten alloy from reaching the focusing lens surface.

9. The probe of claim 1, further comprising a flange to support the holder.

10. The probe of claim 9, wherein the flange comprises aluminum.

11. The probe of claim 1, wherein a flowmeter is connected to the gas valve.

12. The probe of claim 1, further comprising:
a flowmeter to control an inlet flow of the gas from the holder.

13. The probe of claim 1, wherein the gas comprises nitrogen.

14. The probe of claim 1, wherein the gas comprises a nitrogen-argon helium gas.

15. The probe of claim 1, wherein the gas comprises argon.

16. The probe of claim 1, wherein the gas comprises helium.

17. The probe of claim 12, wherein the molten alloy has a surface, and
wherein the inlet and outlet flows of the gas are adjusted so as to locate the molten alloy surface at a focal plane of the focusing lens.

18. The probe of claim 1, wherein the molten alloy comprises one selected from a group consisting of glass, steel, and aluminum.

19. The probe of claim 1, wherein the holder contains the collimating lens with a spiral lock ring that provides fine adjustment of a distance between an output end of the optical fiber and the collimating lens.

20. The probe of claim 1, wherein the holder has a bottom end, the probe further comprising:
a spacer connected to the bottom end of the holder, the spacer having an internal diameter that is equal to an outer diameter of the holder and a female thread that fits into the male thread of the holder, wherein the spacer provides distance adjustment between the focusing lens and the molten alloy surface to focus the laser beam at a selected location on the molten alloy surface.

21. The probe of claim 20, wherein the spacer comprises stainless steel.

22. The probe of claim 1, wherein the holder comprises stainless steel.

23. A fiber optic laser-induced breakdown spectroscopy sensor, comprising:
a laser light source generating laser light;
a harmonic separator for directing the laser light from the laser light source;
a dichroic mirror for reflecting the laser light from the harmonic separator;
a coupling lens for coupling the laser light at an input end of a multimode optical fiber;
a connector for coupling the laser light from an output end of the multimode optical fiber to an input end of a high temperature holder, the high temperature holder comprising optical lenses for collimating and focusing the laser light in a molten alloy to produce a plasma, and for collecting and transmitting an emission signal to the multimode optical fiber; and
a detector portion for receiving the emission signal and analyzing the laser-induced breakdown spectroscopy spectra intensities of the emission signal.

24. The sensor of claim 23, wherein the multimode optical fiber has a silica core and silica cladding.

25. The sensor of claim 23, wherein the high temperature holder comprises stainless steel.

26. The sensor of claim 23, wherein the connector comprises stainless steel.

27. The sensor of claim 23, wherein the detector portion includes a detector, the detector being selected from a group consisting of a charge coupled detector and an intensified charge coupled detector.

28. The sensor of claim 23, wherein the dichroic mirror transmits wavelengths in a range of about 180–1,000 nm and reflects wavelengths in a range of about 500–540 nm.

29. The sensor of claim 23, wherein the laser light source is a neodymium yttrium-aluminum garnet laser source.

30. The sensor of claim 23, wherein the dichroic mirror is positioned at about a 45° angle relative to a line between the detector portion and a sample to be analyzed.

31. The sensor of claim 23, wherein the coupling lens has a focal length of about 10 cm.

32. The sensor of claim 23, wherein the laser light source has a maximum pulse energy of about 180 mJ.

33. The sensor of claim 23, wherein the multimode optical fiber has a numerical aperture of about 0.16.

34. The sensor of claim 23, wherein the multimode optical fiber includes a first end and a second end, the sensor further comprising:
stainless steel fiber connectors located at the first end and the second end of the multimode optical fiber.

35. The sensor of claim 23, wherein the multimode optical fiber has a core diameter of about 1.0 mm.

36. The sensor of claim 23, wherein the optical lenses include a plano convex fused silica collimating lens having a focal length of about 10 cm.

37. The sensor of claim 36, wherein the optical lenses include a plano convex fused silica focusing lens having a focal length of about 7.62 cm.

38. The sensor of claim 37, wherein the high temperature holder further comprises an internal snap ring for preventing movement of the focusing lens.

39. The sensor of claim 37, wherein the collimating lens and the focusing lens are separated by at least 2 m.

40. The sensor of claim 23, wherein the high temperature holder includes a gas valve for controlling flow of a purging gas to cool the lens holder.

41. The sensor of claim 23, wherein the multimode optical fiber is used for transmitting the laser light to the molten alloy and for transmitting the emission signal to the detector portion.

42. The sensor of claim 23, further comprising:
a spacer connected to the bottom end of the high temperature holder.

43. The sensor of claim 23, further comprising:
a beam dump for absorbing the laser light passing through the harmonic separator.

44. The sensor of claim 23, wherein the detector portion includes at least one selected from a group consisting of a spectrometer, an intensified charged couple device, a controller, a pulse generator, and a processor.

45. The sensor of claim 44, wherein the processor is selected from a group consisting of a personal computer, a minicomputer, a microcomputer, and a main frame computer.

* * * * *